United States Patent
Broberg et al.

(12)

(10) Patent No.: US 6,764,308 B1
(45) Date of Patent: Jul. 20, 2004

(54) SURGICAL DEVICE

(75) Inventors: Leif Broberg, Mölndal (SE); Lars Narhed, Eslöv (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/230,428

(22) PCT Filed: Dec. 15, 1998

(86) PCT No.: PCT/SE98/02319

§ 371 (c)(1),
(2), (4) Date: Jan. 26, 1999

(87) PCT Pub. No.: WO94/09719

PCT Pub. Date: May 11, 1994

(30) Foreign Application Priority Data

Dec. 17, 1997 (SE) .............................. 9704715

(51) Int. Cl.[7] .............................................. A61C 3/00
(52) U.S. Cl. .................................................... 433/157
(58) Field of Search .................. 433/149, 117, 433/159, 141, 162, 163; 81/440; 7/165, 118, 128

(56) References Cited

U.S. PATENT DOCUMENTS

| 234,540 A | * | 11/1880 | Collins | 81/440 |
|---|---|---|---|---|
| 317,318 A | * | 5/1885 | Davis | 81/440 |
| 385,791 A | * | 7/1888 | Carpenter | 81/440 |
| 1,662,461 A | * | 3/1928 | Klaboe | 81/440 |
| 4,384,499 A | * | 5/1983 | Shockley | 81/440 |
| 4,521,187 A | | 6/1985 | Casper | 433/72 |
| 5,078,600 A | | 1/1992 | Austin | 433/73 |
| 5,926,885 A | * | 7/1999 | Williams | 7/165 |
| 5,974,677 A | * | 11/1999 | Butwin | 33/463 |
| 6,049,990 A | * | 4/2000 | Holland | 33/464 |

FOREIGN PATENT DOCUMENTS

| FR | 2371912 | 6/1978 |
|---|---|---|
| WO | 9409719 | 5/1994 |

* cited by examiner

Primary Examiner—Nicholas D. Lucchesi
(74) Attorney, Agent, or Firm—White & Case LLP

(57) ABSTRACT

Surgical device (1) for use in a surgical procedure comprising a plurality of surgical instruments (3a, 3b, 3c) for performing predetermined steps of the surgical procedure with at least one of the surgical instruments being movable relative to the other surgical instruments of the device.

7 Claims, 1 Drawing Sheet

SURGICAL DEVICE

FIELD OF THE INVENTION

Figure 1:
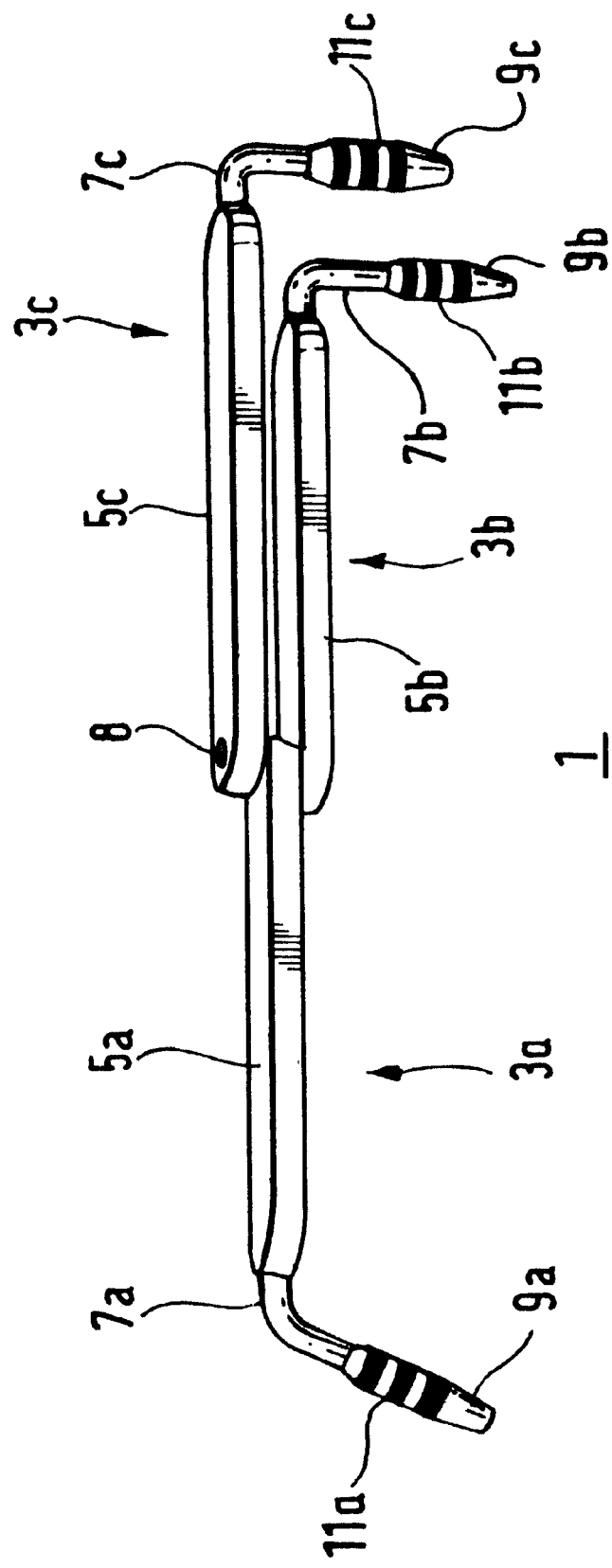

The present invention relates to a surgical device for use in a surgical procedure and is particularly, but not exclusively, concerned with a surgical device for use in a surgical procedure for implanting a prosthesis structure into a bone tissue structure, for example implanting a dental prosthesis structure into a jaw bone of a human or animal patient.

BACKGROUND OF THE INVENTION

Dental prosthesis structures typically comprise an anchoring component or fixture which is anchored in the bone tissue of the jaw bone, a spacer component or abutment which is attached to the anchoring component to bridge the soft tissue layer overlying the jaw bone and a restoration component such as a bridge or crown supported on the spacer component.

A variety of different surgical instruments are needed by the dental surgeon for implanting the prosthesis structure, for example drills, bone taps, probes, wrenches, depth gauges etc. It would obviously be convenient for the surgeon to have some of these instruments connected together rather than separate, particularly in the case of related instruments or instruments which will be needed in adjacent steps of the surgical procedure.

In Applicant's prior International patent application publication No. WO94/09719 there is made known integrating two different dental implant surgical instruments into a single dental implant surgical device. These two instruments, however, are rigidly connected together so that the dental surgeon needs to maneuver the device around to be able to use the different instruments. It would be further advantageous for the dental surgeon to be able to have such a device in which the instruments are able to be moved relative to one another.

SUMMARY OF THE INVENTION

According to the present invention there is provided a surgical device for use in a surgical procedure comprising a plurality of surgical instruments for performing predetermined steps of the surgical procedure with at least one of the surgical instruments being movable relative to the other surgical instruments of the device.

In an embodiment of the invention all of the surgical instruments are movable relative to each other.

In an embodiment of the invention such as the one hereinafter to be described the surgical device comprises more than two surgical instruments with each surgical instrument being independently movable. This may be accomplished as in the embodiment of the invention hereinafter to be described by having each surgical instrument pivotally mounted to the device. For a more compact device the surgical instruments may be pivotally mounted to the device at a common pivot point.

In an embodiment of the invention the surgical procedure comprises a sequence of different predetermined surgical steps and each surgical instrument is for performing a different predetermined surgical step of the surgical procedure.

In an embodiment of the invention the surgical procedure is for implanting a prosthesis structure into a bone tissue structure of a human or animal patient, for instance an orthopaedic prosthesis structure or, as in the embodiment of the invention hereinafter to be described, a dental prosthesis structure.

In an embodiment of the invention the prosthesis structure is a dental prosthesis structure which comprises an anchoring component for anchorage in a bore provided in the bone tissue of a jaw bone, the anchoring component being selected from a set of standard anchoring components of different lengths, and one of the surgical instruments is a depth gauge adapted to be positioned in the bore to enable a standard anchoring component of correct length to be selected from the set for anchorage in the bore.

In an embodiment of the invention such as the one hereinafter to be described the prosthesis structure is a dental prosthesis structure which comprises an anchoring component for anchorage in a bore provided in the bone tissue of a jaw bone and a spacer component for attachment to the anchoring component when anchored in the bore in the jaw bone to bridge the soft tissue layer overlying the anchoring component, the spacer component being selected from a set of standard spacer components of different lengths, and one of the surgical instruments is a depth gauge adapted to engage with the proximal end of the anchoring component when anchored in the bore through the soft tissue layer to enable a standard spacer component of correct length to be selected from the set for attachment to the anchoring component. One of the other surgical instruments could, of course, be a depth gauge for enabling selection of the anchoring component as described in the preceding paragraph.

In an embodiment of the invention the surgical device comprises a handle and the surgical instruments are coupled to the handle.

The present invention further provides a kit of surgical instruments for carrying out a surgical procedure, a plurality of the surgical instruments in the kit forming an integrated surgical device with at least one of the surgical instruments of the surgical device being movable relative to the other surgical instruments of the surgical device.

DETAILED DESCRIPTION OF EXEMPLARY EMBODIMENT

By way of example, an embodiment of the invention will now be described with reference to the accompanying Figure in which there is shown a dental implant surgery device 1 comprising three surgical instruments 3a, 3b, 3c. Each surgical instrument 3a, 3b, 3c is associated with a different fixture and adapted to co-operate therewith to determine which standard abutment in a set of standard abutments having different lengths should be selected for attachment to the associated fixture when anchored in a jaw bone of a patient for the prevailing conditions and the prosthesis requirements, as will be described in more detail hereinafter.

As can be seen, each surgical instrument 3a, 3b, 3c has a shank portion 5a, 5b, 5c and a head portion 7a, 7b, 7c with the shank portions 5a, 5b, 5c being connected to one another through a common pivot point 8 whereby each surgical instrument is independently pivotable about the other two surgical instruments. The dental implant surgery device 1 may be modified so that the common pivot point 8 is disposed closer to the head portions 7a, 7b, 7c by making the shank portions 5a, 5b, 5c overlap one another on the side of the common pivot point 8 remote from the head portions 7a, 7b, 7c. This will give a more reinforced section for the dental surgeon to grip to counteract the bending stresses that will be experienced by the dental implant surgery device 1 in use.

The fixtures with which the surgical instruments 3a, 3b, 3c are respectively associated all have a trailing end in which there opens a socket having a conical entrance section and a threaded bore section. Moreover, the boundary walls of the conical entrance sections of the sockets of the respective associated fixtures are inclined at a common angle. The depth of the conical entrance section of the socket of each associated fixture is different, however, due to the trailing end widths of the associated fixtures being different.

Consequent to the design of the sockets of the associated fixtures, each standard abutment in the set has (i) a conical profile which enables it to seat in the conical entrance sections of the sockets of the associated fixtures, and (ii) screw means for screwing into the threaded bore sections of the sockets of the associated fixtures to secure it to the associated fixtures.

To enable each surgical instrument 3a, 3b, 3c to co-operate with the fixture associated therewith the head portions 7a, 7b, 7c are each provided with a conical distal end 9a, 9b, 9c for seating in the conical entrance section of the socket of the associated fixture, each conical distal end 9a, 9b, 9c being sized for the particular depth of the conical entrance section of the socket of the associated fixture. Each surgical instrument 3a, 3b, 3c is thus able to engage with the fixture associated therewith in an analogous manner to the standard abutments.

The head portion 7a, 7b, 7c of each surgical instrument 3a, 3b, 3c is further provided with a series of alternating light and dark, colored circumferential bands 11a, 11b, 11c proximally of the conical distal end 9a, 9b, 9c with the boundary lines between adjacent light and dark coloured bands in each series 11a, 11b, 11c representing standard abutments of different lengths. When the conical distal end 9a, 9b, 9c of one of the surgical instrument 3a, 3b, 3c is seated in the conical entrance section of the socket of the associated fixture, a standard abutment of correct length for the prevailing conditions and prosthesis requirements is able to be selected for attachment to the associated fixture by reference to the disposition of the boundary lines in the series of circumferential band 11a, 11b, 11c relative to the margin of the soft tissue layer overlying the jaw bone at the fixture site. Further details on the abutment depth gauge function of the head portions 7a, 7b, 7c can be gathered from WO94/09719 supra the contents of which relating to this feature are incorporated herein by reference.

It may be the case that the conical entrance sections of the sockets of the fixtures associated with the surgical instruments 3a, 3b, 3c differ from one another in the angle of inclination of their boundary walls in which case there would be (i) a different set of standard abutments for each associated fixture, the standard abutments in each set having a conical profile matched to the conical entrance section of the socket of the associated fixture, and (ii) a different profile for the conical distal ends 9a, 9b, 9c, each matched to the conical entrance section of the socket of the associated fixture.

It will be clear that the surgical device of the invention need not necessarily be composed of instruments used for the same function as in the illustrated embodiment but could easily be modified so as to include or be composed of a variety of different dental implant surgery instruments, for example probes, bone taps, wrenches, fixture depth gauges etc. It will further be clear that the present invention is not restricted to the field of implant surgery but has application in the broader field of surgery per se.

What is claimed is:

1. A surgical device consisting essentially of a plurality of depth gauges for implanting a dental prosthesis in a jaw bone of a patient, wherein each depth gauge comprises a shank portion and a bead portion having one or more depth indicator marks, and wherein the shank portions are pivotally mounted relative to each other.

2. The surgical device according to claim 1, wherein the depth gauges are movable relative to each other.

3. The surgical device according to claim 1, wherein at least one of the depth gauges is movable relative to the other depth gauges.

4. The surgical device according to claim 1, wherein the surgical instruments are pivotally mounted at a common pivot point.

5. The surgical device according to claim 1, wherein the dental prosthesis structure comprises an anchoring component for anchorage in a bore provided in the bone tissue of the jaw bone, the anchoring component being selected from a set of standard anchoring components of different lengths, and wherein each depth gauge is adapted to be positioned in the bore to enable a standard anchoring component of correct length to be selected from the set for anchorage in the bore.

6. The surgical device according to claim 1, wherein the dental prosthesis structure comprises an anchoring component for anchorage in a bore provided in the bone tissue of the jaw bone and a spacer component for attachment to the anchoring component when anchored in the bore in the jaw bone to bridge the soft tissue layer overlying the anchoring component, the spacer component being selected from a set of standard spacer components of different lengths, and wherein each depth gauge is adapted to engage with the proximal end of the anchoring component when anchored in the bore through the soft tissue layer to enable a standard spacer component of correct length to be selected from the set for attachment to the anchoring component.

7. A kit of surgical instruments for carrying out a surgical procedure for implanting a dental prosthesis structure in a jaw bone of patient in which the surgical instruments in the kit form an integrated surgical device consisting essentially of a plurality of depth gauges, wherein each depth gauge comprises a shank portion and a head portion having one or more depth indicator marks, and wherein the shank portions are pivotally mounted relative to each other.

* * * * *